(12) United States Patent
Ruiz et al.

(10) Patent No.: US 7,803,738 B2
(45) Date of Patent: Sep. 28, 2010

(54) CONCENTRATED HERBICIDE FORMULATION, NON-VOLATILE, STABLE AT LOW TEMPERATURES AND SOLUBLE IN WATER OF 2,4-D [(2,4-DICHLOROPHENOXY)ACETIC] ACID

(75) Inventors: Martha María del Carmen Ruiz, Buenos Aires (AR); Oscar Pratto, Buenos Aires (AR)

(73) Assignee: Atanor S.A., Beunos Aires (AR)

( * ) Notice: Subject to any disclaimer, the term of this patent is extended or adjusted under 35 U.S.C. 154(b) by 419 days.

(21) Appl. No.: 10/992,683

(22) Filed: Nov. 22, 2004

(65) Prior Publication Data
US 2005/0215434 A1    Sep. 29, 2005

(30) Foreign Application Priority Data
Nov. 24, 2003    (AR)    ............................... P030104341

(51) Int. Cl.
*A01N 37/00*    (2006.01)
*A01N 39/02*    (2006.01)

(52) U.S. Cl. ...................... 504/307; 504/323
(58) Field of Classification Search .................. 504/323
See application file for complete search history.

(56) References Cited

U.S. PATENT DOCUMENTS

| 2,471,575 A | 5/1949 | Manske | ...................... 260/521 |
| 6,010,979 A * | 1/2000 | Osborn et al. | ............... 504/206 |
| 6,770,594 B2 * | 8/2004 | Bickers et al. | .............. 504/212 |

FOREIGN PATENT DOCUMENTS

GB    573476    11/1945

OTHER PUBLICATIONS

Matsumoto et al. "Effect of humectants on pesticide uptake through plant leaf surfaces". Chapter 25 in Adjuvants for Agrichemicals, Chester L. Foy, ed. CRC Press. p. 261-271. 1992.*

* cited by examiner

*Primary Examiner*—Alton N Pryor
(74) *Attorney, Agent, or Firm*—Jacobson Holman PLLC

(57) ABSTRACT

Concentrated herbicide formulation, non-volatile, stable at low temperatures and soluble in water of 2,4-D acid ((2,4-dichlorophenoxy) acetic acid), characterized in that it includes:

45 to 75%, w/v of 2,4-D acid, in the form of a water soluble salt of a primary, secondary, or tertiary amine, or a primary, secondary, or tertiary alkanolamine, or a mixture of both;

1 to 40%, w/v of a humectant selected from a group made up of amine oxides, amide amine oxides, ethoxylated fatty amines, glycerin and its derivatives, sorbitol and its derivatives and polyethyleneglycol, and their mixtures;

0.1 to 20%, w/v of an antifreeze selected from a group made up of glycols;

0.01 to 0.5%, w/v of an antifoaming agent chosen from amongst silicon oil emulsions at 10-30%, surfactant agents based on hydrocarbons such as fatty acids and their salts in hydrocarbon, and alcohols with 8 or more carbon atoms, such as 2-ethylhexanol and isooctanol;

optionally, 0.5-10%, w/v of a non-polar solvent; and the rest being water.

11 Claims, No Drawings

CONCENTRATED HERBICIDE FORMULATION, NON-VOLATILE, STABLE AT LOW TEMPERATURES AND SOLUBLE IN WATER OF 2,4-D [(2,4-DICHLOROPHENOXY)ACETIC] ACID 2,4-D acid is an herbicide whose preparation and properties have been known for several decades, for example, from the publications J. Am. Chem. Soc. 63, 1768 (1941), GB 573, 476 (1945) and U.S. Pat. No. 2,471,575 (1949).

This compound has the following chemical name and structural formula:

[see source for formula]

(2,4-dichlorophenoxy) acetic acid and may be applied in the form of alkaline salts (of sodium or potassium), amine salts (with dimethylamine, isopropylamine, triethylamine, diethanolamine), and esters (isopropyl, butyl, etc).

2,4-D is an herbicide selective for dicotyledons, which can be applied in areas planted with corn, wheat, rice, and other grains in order to eliminate a great variety of weeds without affecting the crop in any way.

2,4-D acid works on undesired plants by breaking the balance between the synthesis and use of carbohydrates.

After one application of 2,4-D, with the doses usually used for herbicide treatment, a speeding up of all the plant's functions is observed; however, the speed of photosynthesis is less, which causes the plant to start consuming its reserves more rapidly than it synthesizes them.

As this process continues, the speed of the respiration of the plant starts decreasing, photosynthesis slows down, and the plant gradually drains its reserves until it finally dies.

2,4-D acid is a white, crystalline solid, minimally soluble in water, generally formulated as soluble concentrates or emulsifiable concentrates, in order to facilitate its application.

The soluble concentrates of this compound contain its sodium, potassium, or ammonium salts (less soluble), useful for high volume applications but contraindicated for low volume spraying. The non-volatile salts of amines or alkanolamines with high polarity and solubility are also useful.

In turn, emulsifiable concentrates of 2,4-D acid may contain its high volatility esters, such as ethyl, propyl, isopropyl, butyl, isobutyl, or amyl esters, or its low volatility esters such as octyl or butoxyethyl esters.

The foliar epidermis is covered by a layer called the cuticle, formed by a waxy film with low polarity.

The amines and alkanolamines are highly polar compounds that are not compatible with this waxy layer covering the leaf surface.

Consequently, when an amine compound is applied on this apolar surface, drops of water remain, forming small spheres that barely touch the surface of the leaves at one point, or even slide on them.

In turn, the esters of 2,4-D are minimally polar compounds, which makes them directly compatible with the way layer covering the leaf surface, favoring dissolution of the waxy layer. Thus, the 2,4-D herbicide in the form of its non-polar esters can penetrate plants more easily than in the form of its amine salts.

It has been confirmed that, with the same acid equivalent, the esters are more effective than the amines (concerning penetration) although their herbicidal effect is slower. On the contrary, the amines have faster herbicidal efficacy than the esters but, as has been indicated, they are less effective than the esters as to the ease of absorption on the leaves.

In turn, low volatility esters require a longer time to penetrate through the cuticle than more volatile esters; however, this volatility is a serious drawback for the surrounding biological environment (animals and plants) that may be negatively affected by the intrinsic deleterious effect of the herbicide.

As indicated above, the amines act more quickly in the plant, but penetrate more slowly. However, amine salts have the advantage of not being volatile, and therefore do not have the risks of the esters of deviating due to the volatility, which may damage sensitive crops nearby.

However, since the amine and alkanolamine salts of 2,4-D acid are more suitable, from the viewpoint of their herbicidal efficacy and the care of the environment than the corresponding esters of 2,4-D acid, it is necessary to have formulations of 2,4-D acid in the form of amine salts which solve the technical problem of deficient absorption of the herbicide on the leaves of treated weeds.

Taking into consideration these shortcomings currently seen with formulations of 2,4-D based on amine salts, this invention proposes a new herbicide formulation of 2,4-D acid based on amine salts which solves the problems presented by such salts due to its penetration power, by addition of specific coadjuvants which improve the performance of the active herbicide compound while also stabilizing said formulation at temperatures of −8±2° C.

DETAILED DESCRIPTION OF THE INVENTION

The invention concerns an herbicide formulation as a soluble aqueous concentrate containing a salt of the 2,4-D acid, such as an amine or alkanolamine salt or a mixture of both, one ore more humectants, an antifreeze, and anti-foaming agent and a solvent.

More specifically, this invention refers to a concentrated herbicide formulation, non-volatile, stable at low temperatures and soluble in water of 2,4-D ((2,4- dichlorophenoxy) acetic acid) which includes:

- 45 to 75%, w/v 2,4-D acid, in the form of a water-soluble salt of a primary, secondary, or tertiary amine, or a primary, secondary, or tertiary alkanolamine, or a mixture of both;
- 1 to 40%, w/v of a humectant selected from a group made up of amine oxides, amide amine oxides, ethoxylated fatty amines, glycerin and its derivatives, sorbitol and its derivatives and polyethyleneglycol, and their mixtures;
- 0.1 t0 20%. w/v of an antifreeze selected from a group made up of glycols;
- 0.01 to 0.5% w/v of an antifoaming agent chosen among silicon oil emulsions at 10-30%, surfactant agents based on hydrocarbons such as fatty acids and their salts in hydrocarbon, and alcohols with 8 or more carbon atoms, such as 2-ethylhexanol and isooctanol;
- optionally, 0.5-10%, w/v of a non-polar solvent; and
- the rest being water.

In a preferred embodiment, the formulation of this invention contains 48 to 72%, w/v of 2,4-D acid, said acid being present as amine salt of alkanolamine salt or a mixture of both.

In the formulations of this invention, the humectant agent is preferably at 2 to 30% w/v and is an ethoxylated fatty amine or dimethyl laurylamine oxide.

The preferred antifreeze agent is ethyleneglycol and it is preferably present in 0.5 to 15% w/v of the formulation.

As antifoaming agent, the use of a silicon oil in a quantity ranging between 0.01 and 0.5%, w/v of the formulation, is preferred.

General Procedure for Preparation of the Formulations of the Invention

The general method for preparing the herbicidal formulations of this invention includes the following stages:

In a reactor equipped with refrigeration, stirring, thermocouple, and electrode for determining pH, we load approximately 80% of the water needed for the formulation, the humectant or humectants, the antifreeze, the anti-foaming agent, and the solvent.

Then alternatively and slowly we add the 2,4-D acid and the amine or alkanolamine, or the mixture of both, always adding a little excess acid in order to prevent the excessive amine odor.

Since the neutralization reaction is exothermic, stirring and refrigeration with water must be permanently maintained, checking that the temperature does not exceed 50° C.

When the stoichiometric addition of 2,4-D acid and amine and/or alkanolamine is completed, we adjust the pH to a value ranging between 7.5 and 8.5 by adding the same amine and/or alkanolamine, and then fill to volume with demineralized water.

We determine the titer of the active compound ((2,4-D dichlorophenoxy) acetic acid) by HPLC chromatography and adjust the formulation to the desired concentration of 2,4-D acid by adding demineralized water.

EXAMPLES OF PREPARATION OF FORMULATIONS OF THE INVENTION

Example 1

In a 2-liter round bottom flask equipped with stirring, thermocouple, electrode and amine measuring device, the following were added: 224 g of water, 144 g of diethanolamine at 98% by weight, and 50 g of ethoxylated fatty amine with 15 moles of ethylene oxide (for example "Ultramine from Oxiteno") and 15 g of ethyleneglycol.

Next, the following were slowly and alternately added: 617 g of 2,4-D acid at 97% by weight and 101 g of dimethylamine at 60% by weight. When the reagents were completely added, the pH was adjusted to 8 by dimethylamine and demineralized water was added to make 1 liter of the formulation.

Example 2

In a round-bottom flask similar to example 1, the following were added: 224 g of water, 72 g of diethanolamine at 98% by weight, 40 g of dimethyl laurylamine oxide, 10 g pf ethyleneglycol, and 0.4 g of anti-foaming agent. Next, the following were slowly added: 617 g of 2,4-D acid at 97% by weight and 154 g of dimethylamine at 60% by weight.

When the reagents were completely added, the pH was adjusted to 8.5 by diethanolamine and then demineralized water was added to make 1 liter of the formulation.

Example 3

Steps were taken as in Example 2, adding an additional 50 g of N-methylpyrrolidione before adding the main reagents.

Example 4

Steps were taken as in Example 1, but instead of adding 144 g of diethanolamine, 207 g of triethanolamine at 98% by weight was added.

Field Tests

Evaluation of the Efficacy of Different Formulations and Doses of 2,4-D Amine Salt 60% Versus 2,4-D Ester Location of the field tests: EEA Manfredi (NATIONAL INSTITUTE OF AGRO-LIVESTOCK TECHNOLOGY-CORDOBA REGIONAL CENTER)

Experimental design: random blocks

Number of repetitions: 3

Lot size: 5×3 m

Soil type: Typic Haplustoll, fine-loamy texture

Percentage of organic material in the soil: 3% in the superficial horizon (10 cm) and 2.5 up to 20 cm of depth Soil pH: 6.5

Application type: total coverage

Application date: February 2003

Application time: 3:00 PM to 5:00 PM

Air temperature: 33° C. at 3:00 PM; 31° C. at 4:55 PM

Soil temperature: 28.5° C. at 3:00 PM; 25° C. at 4:55 PM

Ambient relative humidity: 52% at 3:00 PM, 56% at 4:55 PM

Soil humidity: regular but the weeds in general were young and in good vegetative condition Wind speed (Km/h): 3 to 6 at 3:15 PM; 0 to 3 at 4:30 PM Type of weeds: Mallow mainly and in lesser quantity stramonium, quinoa, sow thistle, and euphorbia Applicator equipment: manual traction with carbon dioxide pressure source Application speed: 1 m/s Type of tablet: DG 11002 (antidrift)

Sprayer boom height: 0.6 m

Space between nozzles 0.7 m

Number of nozzles: 5

Application strip: 3.0 m

Flow applied: 170 l/ha

Working pressure: 35 lbs/inch$^2$

The treatments applied with the product formulated were as follows:

| Treatment | Dose 1/ha |
|---|---|
| Isobutyl ester of 2,4-D 100% w/v | 0.6 |
| Dimethylamine salt of 2,4-D | 0.8 |
| 60% w/v as 2,4-D acid, Blank | 1.0 |
| Sample | 1.2 |
| Amine salt of 2,4-D | 0.8 |
| 60% w/v as 2,4-D acid | 1.0 |
| Example 2 | 1.2 |
| Amine salt of 2,4-D | 0.8 |
| 60% w/v as 2,4-D acid | 1.0 |
| Example 3 | 1.2 |

Note:

1 liter of isobutyl ester of 2,4-D equivalent to 774 g of 2,4-D acid 1 liter of amine salt 60% w/v equivalent to 600 g of 2,4-D acid Blank Sample: amine salt 60% w/v without addition of additives Percentage of total coverage of weeds and density and height by control species at the time of application:

| Treatment | Coverage | MALCO No. of plants/ m² | MALCO Height in cm | CHEAL No. of plants/ m² | CHEAL Height in cm | DATFE No. of plants/ m² | DATFE Height in cm | EUPSS No. of plants/ m² | EUPSS Height in cm | SONOL No. of plants/ m² | SONOL Height in cm |
|---|---|---|---|---|---|---|---|---|---|---|---|
| Weed coverage test | 38.3 | 56.6 | 14.7 | 2.7 | 10.3 | 2.7 | 16.0 | 7.3 | 12.6 | 5.0 | 8.0 |

References:
Malco: *Malvastrum coromandelianum*
Cheal: *Chenopodium album*
Datfe: *Datura feroz*
Eupss: *Euphorbia* sp.
Sonol: *Sonchus oleraceus*
Coverage: percentage of weeds per square meter References Malco: *Malvastrum coromandelianum*
Cheal: *Chenopodium album*
Datfe: *Datura feroz*
Eupss: *Euphorbia* sp.
Sonol: *Sonchus oleraceus*
Coverage: percentage of weeds per square meter Results Obtained

TABLE 1 percentages of total control by treatment and species by species at 7 DAA

| Treatment | Dose | Control | MALCO | CHEAL | DATFE | EUPSS | SONOL |
|---|---|---|---|---|---|---|---|
| Isobutyl ester of 2,4-D | 0.6 | 79.0a | 79.0a | 85.0 | 71.7 | 68.3b | 85.0ab |
| Dimethylamine salt of 2,4-D 60% w/v | 0.8 | 78.3a | 78.3a | 83.3 | 70.0 | 50.0a | 81.7a |
|  | 1.0 | 81.7ab | 81.7ab | 85.0 | 76.7 | 66.7 | 81.7a |
|  | 1.2 | 83.3ab | 83.3abc | 85.0 | 75.0 | 66.7b | 81.7a |
| Amine salt of 2,4-D 60% w/v Example 2 | 0.8 | 83.3ab | 83.3ab | 88.3 | 78.3 | 68.3b | 86.7ab |
|  | 1.0 | 84.3ab | 85.0abc | 86.7 | 75.0 | 65.0b | 85.0ab |
|  | 1.2 | 88.7b | 89.3c | 88.3 | 78.3 | 73.3b | 88.3b |
| Amine salt of 2,4-D 60% w/v Example 3 | 0.8 | 85.0ab | 85.0abc | 86.7 | 75.0 | 65.0b | 85.0ab |
|  | 1.0 | 81.7ab | 81.7ab | 86.7 | 75.0 | 71.7b | 83.3ab |
|  | 1.2 | 87.8b | 87.8bc | 90.0 | 80.0 | 71.7b | 83.3ab |
| CV % |  |  | 4.5 | 4.6 | 3.7 | 4.9 | 9.8 | 3.8 |

(*) DAA: days after applications

Different letters indicate significant difference ($P \leq 0.05$) according to Duncan's test.

Percentages of total coverage and coverage and height by species in the control at 7 DAA (*)

| Treatment | Coverage | MALCO Coverage % | MALCO Height in cm | CHEAL Coverage % | CHEAL Height in cm | DATFE Coverage % | DATFE Height in cm | EUPSS Coverage % | EUPSS Height in cm | SONOL Coverage % | SONOL Height in cm |
|---|---|---|---|---|---|---|---|---|---|---|---|
| Weed coverage test | 46.7 | 33.3 | 19.3 | 3.3 | 18.0 | 5.3 | 24.7 | 4.3 | 15.0 | 2.0 | 10.0 |

TABLE 2 percentage of total control by treatment and species at 14 DAA

| Treatment | Dose | Control | MALCO | CHEAL | DATFE | EUPSS | SONOL |
|---|---|---|---|---|---|---|---|
| Isobutyl ester of 2,4-D | 0.6 | 90.0b | 91.7abc | 90.0 | 81.7 | 68.3 | 90.7 |
| Dimethylamine salt of 2,4-D 60% w/v | 0.8 | 85.0a | 87.7a | 90.0 | 76.6 | 66.7 | 90.0 |
|  | 1.0 | 90.7b | 91.7abc | 93.3 | 83.3 | 73.3 | 89.0 |
|  | 1.2 | 92.3b | 93.7bc | 92.7 | 81.7 | 73.3 | 91.7 |
| Amine salt of 2,4-D 60% w/v Example 2 | 0.8 | 91.3b | 91.7abc | 93.3 | 83.3 | 71.7 | 91.7 |
|  | 1.0 | 92.7b | 94.0c | 91.7 | 86.7 | 75.0 | 93.3 |
|  | 1.2 | 95.0b | 95.7c | 95.7 | 86.7 | 80.0 | 95.0 |
| Amine salt of 2,4-D 60% w/v Example 3 | 0.8 | 90.3b | 89.3ab | 91.7 | 83.3 | 75.0 | 91.7 |
|  | 1.0 | 91.3b | 92.0abc | 90.0 | 83.3 | 73.3 | 91.7 |
|  | 1.2 | 93.3b | 93.7bc | 91.7 | 85.0 | 76.7 | 93.3 |
| CV % |  | 3.0 | 2.5 | 3.0 | 4.3 | 6.5 | 3.8 |

CV% (coefficient of variation percentage): the coefficient of variation eliminates the dimensionality of the variables (e.g.: control %, yield in Kg/ha, number of weeds/m$^2$, etc.) and takes into consideration the existing ratio between means and standard deviation. CVs help in comparing the variability of two sets (samples or populations. Coefficients less than 15-20% are suitable, while higher values indicate distortions in data and therefore less reliable conclusions.

Different letters indicate significant differences ($P \leq 0.05$) according to Duncan's test Coverage and week height were not measured at 14 DAA since their condition was similar to that at 7 DAA, due to the lack of rain which hindered normal weed growth.

Analysis of the Results

Only those species that were present in all lots, even if in low proportion, were considered.

At 7 DAA, the general control of all species with most treatments exceeded 70%, with the exception of the blank formulation doses and the ester 100% formulation dose.

I Malvastrum Coromandelianum (MALCO), the main weed, was controlled up to 88-89% by the formulations according to the invention (Examples 2 and 3), a level that was significantly above the control achieved by the Blank formulations and the isobutyl ester of 2,4-D.

In addition, the formulations according to the invention similarly controlled *Chenopodium album* (CHEAL) and *Datura feroz* (DATFE), although the degree of control over the latter species was lower, raging between 70 and 80% of control, but always with control values greater than those obtained with the treatments carried out with the Blank formulation and that corresponding to the 2,4-D ester.

The most difficult to control weed for all formulations of 2,4-D was *Euphorbia* sp (EUPSS), whose greatest control was 73.3% with the formulation according to this invention (Example 2).

*Sonchus oleraceus* (SONOL) was controlled with values that exceeded 80% with formulations according to this invention (Example 2).

At 14 DAA in all treatments, a 90% or greater increase in weed control was seen when the species were evaluated together (Table 2, first column). Only the lower dose of the blank formulation had a significantly lower effect than the rest.

In general, the 2 formulations of 2,4-D amine salt 60% (Examples 2 and 3) were effective in doses of 0.8, 1.0, and 1.2 l/ha and always with control values greater than those obtained with the Blank formulations and the 2,4-D ester.

The invention claimed is:

1. A concentrated herbicide formulation of 2,4-D acid ((2,4-dichlorophenoxy) acetic acid), said formulation being non-volatile, stable at temperatures of −8±2° C., and soluble in water, characterized in that it comprises:

45 to 75% w/v of 2,4-D acid salt in the form of a mixture of diethanolamine or triethanolamine and dimethylamine water soluble salts;

1 to 40%, w/v of a humectant selected from the group consisting of ethoxylated fatty amines with 15 moles of ethylene oxide or dimethyl laurilamine oxide;

0.1 to 20%, w/v of ethylenylycol as an antifreeze agent;

0.01 to 0.5%, w/v of silicon oil as an antifoaming agent; and the rest being water.

2. The formulation according to claim 1, characterized in that it contains 48 to 72%, w/v of 2,4-D acid.

3. The formulation according to claim 1, characterized in that in the formulation 100% of the acid is present as a mixture of diethanolamine or triethanolamine and dimethylamine water soluble salts.

4. The formulation according to claim 1, characterized in that the humectant is an ethoxylated fatty amine with 15 moles of ethylene oxide.

5. The formulation according to claim 1, characterized in that the humectant is dimethyl laurylamine oxide.

6. The formulation according to claim 1, characterized in that it contains 2 to 30%, w/v of the humectant agent.

7. The formulation according to claim 1, characterized in that it contains 0.5 to 15%, w/v of ethyleneglycol as antifreeze agent.

8. The formulation according to claim 1, characterized in that it contains 0.01 to 0.5%, w/v of a silicon oil as antifoaming agent.

9. The formulation according to claim 1, characterized in that it further contains a non-polar solvent in a concentration ranging between 0.5 and 10% w/v.

10. The formulation according to claim 1, characterized in that it further contains a non-polar solvent selected from a group made up of N-methylpyrrolidone, isophorone, hexylcellosolve, and mixtures of said solvents.

11. A concentrated herbicide formulation of 2,4-D acid ((2,4-dichlorophenoxy) acetic acid), said formulation being non-volatile, stable at temperatures of −8±2° C., and soluble in water, characterized in that it consists of:

45 to 75% w/v of 2,4-D acid salt in the form of a mixture of diethanolamine or triethanolamine and dimethylamine water soluble salts;

1 to 40%, w/v of a humectant selected from the group consisting of ethoxylated fatty amines with 15 moles of ethylene oxide or dimethyl laurilamine oxide;

0.1 to 20%, w/v of ethylenylycol as an antifreeze agent;

0.01 to 0.5%, w/v of silicon oil as an antifoaming agent; and the rest being water.

* * * * *